(12) United States Patent
Emerson et al.

(10) Patent No.: US 6,546,930 B1
(45) Date of Patent: Apr. 15, 2003

(54) BI-LEVEL FLOW GENERATOR WITH MANUAL STANDARD LEAK ADJUSTMENT

(75) Inventors: Paul F. Emerson, St. Louis Park, MN (US); Bradley J. Bonnette, Minneapolis, MN (US); Gary L. Hansen, Eden Prairie, MN (US)

(73) Assignee: Mallinckrodt Inc., St. Louis, MO (US)

( * ) Notice: Subject to any disclaimer, the term of this patent is extended or adjusted under 35 U.S.C. 154(b) by 170 days.

(21) Appl. No.: 09/672,955

(22) Filed: Sep. 29, 2000

(51) Int. Cl.[7] .......................... A61M 16/00; A62B 7/00; F16K 31/02
(52) U.S. Cl. ........................ 128/204.21; 128/204.23; 128/204.18; 128/205.25
(58) Field of Search .................. 128/204.23, 204.18, 128/204.21, 202.22, 205.11, 205.25, 207.12, 207.13

(56) References Cited

U.S. PATENT DOCUMENTS

| | | | | |
|---|---|---|---|---|
| 4,336,590 A | * | 6/1982 | Jacq et al. ................... | 364/418 |
| 5,065,756 A | * | 11/1991 | Rapoport ................ | 128/204.18 |
| 5,148,802 A | * | 9/1992 | Sanders et al. ......... | 128/204.18 |
| 5,535,738 A | * | 7/1996 | Estes et al. ............. | 128/204.23 |
| 5,535,739 A | * | 7/1996 | Rapoport et al. ....... | 128/204.23 |
| 5,685,296 A | * | 11/1997 | Zdrojkowski et al. . | 128/205.24 |
| 5,692,497 A | * | 12/1997 | Schnitzer et al. ...... | 128/204.21 |
| 5,901,704 A | | 5/1999 | Estes et al. | |
| 5,937,855 A | * | 8/1999 | Zdrojkowski et al. . | 128/205.24 |
| 6,349,724 B1 | * | 2/2002 | Burton et al. .......... | 128/204.18 |
| 6,360,741 B2 | * | 3/2002 | Truschel ................ | 128/202.22 |

FOREIGN PATENT DOCUMENTS

| | | |
|---|---|---|
| WO | 92/11054 | 7/1992 |
| WO | 98/06449 | 2/1998 |
| WO | 98/12965 | 4/1998 |
| WO | 00/37135 | 6/2000 |

* cited by examiner

Primary Examiner—Glenn K. Dawson
Assistant Examiner—Michael Mendoza
(74) Attorney, Agent, or Firm—Rothwell, Figg, Ernst & Manbeck

(57) ABSTRACT

An apparatus for delivering a breathing gas to a patient includes a display, a storage device programmed to hold different purge hole leak profiles for a variety of mask types, and a selection mechanism for selecting one of the profiles so that accurate values of tidal volume, excess leak and peak flow may be calculated and shown on the display. The displayed excess leak value can be used to correct the fit of the mask.

20 Claims, 5 Drawing Sheets

BI-LEVEL FLOW GENERATOR WITH MANUAL STANDARD LEAK ADJUSTMENT

BACKGROUND OF THE INVENTION

1. Field of the Invention

The present invention relates generally to an apparatus for delivering a breathing gas to a patient and, more particularly, to a gas flow generator with manual standard leak adjustment.

2. Description of the Background Art

The sleep apnea syndrome affects some 1% to 5% of the general population and is due to upper airway obstruction during sleep. The direct consequences of sleep apnea are sleep fragmentation, partial cessation of ventilation and oxyhemoglobin desaturation. These in turn translate into daytime somnolence, cardiac arrhythmia, congestive heart failure and a variety of other health as well as cognitive dysfunctions. All of these have secondary social and behavioral effects which can result in increased patient morbidity as well as possible mortality if they are engaged in activities which require alertness (such as driving a car).

The causes of upper airway obstruction are varied but may include anatomical changes leading to a narrowing of the pathway, loss of muscle tone and/or increased weight of the structures. Age and obesity appear to be risk factors suggesting that an excess of soft tissue in the neck may provide sufficient pressure on internal structures to compromise the patency of the airway.

Treatment has involved a variety of surgical interventions including uvulopalatopharyngoplasty, gastric surgery for obesity, maxillo-facial reconstruction or even tracheostomy. All of these procedures have the risk of significant morbidity. A more benign treatment but one which requires some behavioral adjustment is that of nasal continuous positive airway pressure (nCPAP or just CPAP). In its simplest form, this treatment involves applying positive pressure to the airway using an airflow generator to force the passage to remain open. If used consistently during sleep, symptoms of sleep apnea can be successfully mitigated.

Some patients, however, are nonresponsive or noncompliant with CPAP treatment due to its continuous nature. This is especially true if the CPAP prescription pressure is relatively high. For these individuals a bilevel therapy is a more reasonable alternative. Pressure cycles from a high level during inhalation (IPAP) to a low level (EPAP) to facilitate exhalation while at the same time continuing to provide some nominal pressure support. This is also useful for individuals who have some form of compromised respiration such as a weakness of the diaphragm muscle due to disease or spinal injury where continuous pressure may be problematic.

All noninvasive flow generators whether they provide pressures at one level (CPAP), two levels (BiLevel/BiPAP) or multiple levels use a patient interface (typically a mask) which has some type of standard leak. The purpose of the standard leak is to allow carbon dioxide to leave the system and minimize rebreathing. Otherwise, significant tidal volumes would be required to clear the dead space of the hose and mask. The standard leak results from a purge hole (sometimes called an exhaust port or bleed hole) of a given size or numerous smaller holes. The size of these holes is determined by the flow capability of the generator and the desired properties of the mask.

In a home environment, flow generators may be used with minimal feedback to the user. In a hospital environment or sleep laboratory, however, it is desirable to know various measurable characteristics of the user's breathing pattern. Typically these would include: the frequency of breathing, the ratio of the inspiration to expiration time (I:E ratio), the leak in excess of the standard purge hole leak, the tidal volume and the peak inhalation flow. The last three parameters in particular require knowledge of the purge hole leak for their correct calculation.

Various approaches have been used to calculate leak. For example, Estes et. al., (U.S. Pat. No. 5,901,704) discloses a method whereby total leak can be calculated and flow adjusted to compensate on a breath by breath basis. However, there is no discussion of how standard purge hole affects the calculation of tidal volume, excess leak or peak flow, nor do they discuss how multiple standard purge holes may be selected.

In another approach, a look-up table appropriate for a single type of mask has been used. For example, the KS 335 gas flow generator sold by Puritan Bennett contains a lookup table for leak in liters per minute which is indexed by the set pressure. The look-up table is based on a standard 4 mm hole in the mask. Masks with purge holes other than 4 mm would not produce correct readings on the device.

Other manufacturers have provided some type of automatic titration means or procedures such as those described by Brewer et. al (WO00037135). They describe a special "mask fit" mode wherein the device is set to a particular mask-fit test pressure, and the "average flow" being the result of low pass filtering of the airflow is determined. This test pressure may be then stepped through the pressure range of interest and the results stored. This procedure must be repeated when masks are changed.

Others methods such as those disclosed by BerthonJones (WO9806449) estimate the nonlinear conductance of the mask orifice by dividing the average flow by the square root of the instantaneous measured pressure. This method, while versatile, is not accurate since purge hole leak must be estimated.

SUMMARY OF THE INVENTION

In accordance with one aspect of the present invention, an apparatus for delivering a breathing gas to a patient is provided which includes a blower that generates a flow of a breathing gas, a gas flow rate sensor positioned to sense the flow of breathing gas generated by the blower, a memory device containing a plurality of purge hole leak profiles corresponding to specific types of breathing masks, means for selecting one of the plurality of purge hole leak profiles from the memory device, and a microprocessor programmed to calculate at least one of excess leak, tidal volume, and peak flow using a flow rate measured by the gas flow rate sensor and the selected purge hole leak profile.

In accordance with another aspect of the present invention, a method for delivering a breathing gas to a user is provided which includes the steps of generating a flow of a breathing gas using a gas flow generator, measuring the flow rate of the breathing gas, selecting one of a plurality of purge hole leak profiles from a memory device, and calculating at least one of excess leak tidal volume, and peak flow using the measured flow rate and the selected purge hole leak profile.

In the preferred embodiment, the invention includes a display means, a selection means, and a storage means whereby different pressure versus leak curves may be selected for the purpose of calculating the standard leak appropriate to a given mask type. Accurate values of tidal volume, excess leak and peak flow may thereby be advantageously calculated. From the displayed excess leak value the fit of the mask may be corrected.

The above and other features and advantages of the present invention will be further understood from the following description of the preferred embodiments thereof, taken in conjunction with the accompanying drawings in which like numerals denote like parts.

DETAILED DESCRIPTION OF THE PREFERRED EMBODIMENTS

Figure 1:
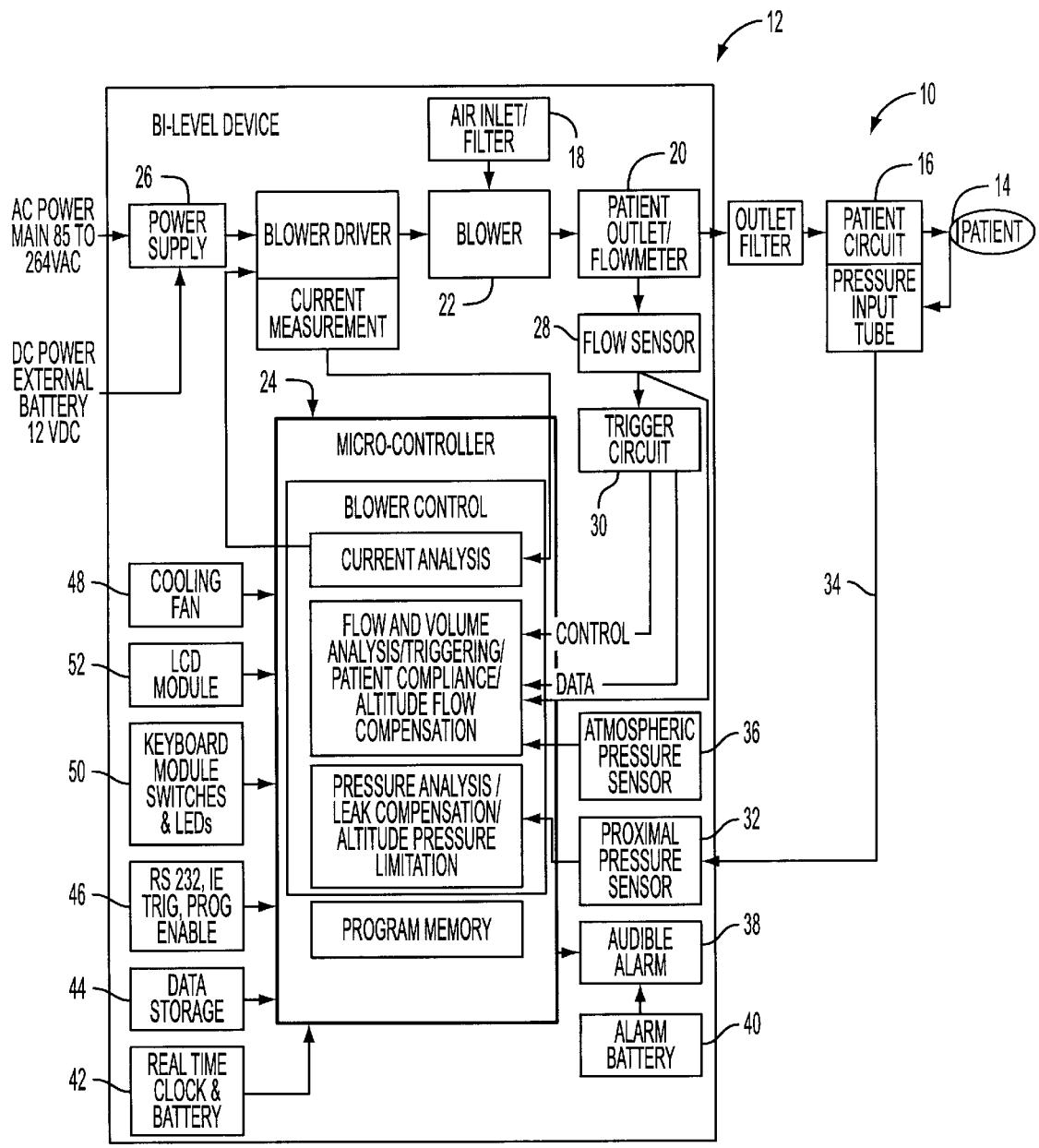
FIG. 1 is a schematic illustration of an apparatus for delivering a breathing gas to a user including a flow generating device according to the present invention.

An apparatus 10 according to an embodiment of the present invention is shown in schematic form in FIG. 1. Apparatus 10 includes a gas flow generator 12 which receives breathing gas from a source and delivers the gas to a breathing appliance 14 via a delivery conduit 16 such as a hose. The breathing gas can be supplied by any suitable source including, by way of example, ambient air or a pressurized bottle containing a breathing gas. The breathing appliance is preferably a mask, but can be any other suitable appliance for interfacing between a source of breathing gas and a patient's respiratory system. The appliance includes an exhaust port or purge hole to purge breathing gases during exhalation. Any suitable purge hole can be used including conventional valve designs and open ports. The purge hole has a standard leak which varies according to gas pressure.

Gas flow generator 12 generally includes a breathing gas inlet 18, a breathing gas outlet 20, a blower 22 receiving breathing gas from the inlet and having an impeller driven by a motor to deliver the gas at a positive pressure to the outlet, and a blower control system 24 including a microcontroller for controlling the pressure of breathing gas in the delivery conduit by adjusting the speed of the blower motor. The gas flow generator preferably also includes a power supply 26 for distributing power from internal or external sources to the blower and blower control system, and a flow rate sensor or flow meter 28, preferably located downstream of the blower, for generating a flow rate signal indicative of the flow of breathing gas from the blower. The flow rate signal from the flow meter is fed to the blower control system and can optionally be fed to a conventional trigger or decision circuit 30 which uses the flow rate signal in a known manner to provide a trigger signal to the blower control system for initiating a change in motor speed for bilevel positive airway pressure therapy.

Gas flow generator 12 is also shown having a proximal pressure sensor 32 communicating with a pressure input tube 34 from patient circuit 14, 16, an atmospheric pressure sensor 36, an audible alarm 38 with battery 40, a clock 42, data storage 44, an external communication port 46, a cooling fan 48, controls 50, and a display device 52.

Leak is typically calculated by averaging flow over the course of a single breath including an inhalation phase and an exhalation phase (EQ 1). Specifically total Leak ($L_T$) is the sum of the instantaneous flows divided by the sum of the time intervals between flow determinations. For low pressures, flow can be negative (into the device upon exhalation) so it is important that the flow transducer be bidirectional $$L_T = \frac{\sum_i F_i}{\sum \Delta t} \quad [1]$$

Total leak is comprised of the excess leak ($L_{EX}$) plus the purge hole leak ($L_P$). The excess leak would be the leak in excess of the purge hold leak and is generally due to a poor mask fit. It is useful to know the amount of this leak so that the mask may be adjusted in order to minimize its value. Consequently, $L_{EX}$ is displayed on many devices rather than $L_T$. $L_{EX}$ is calculated simply by rearranging Eq. 2 so that $L_P$ is subtracted from $L_T$.

$$L_T = L_{EX} + L_P \quad [2]$$

$L_{EX}$ may be calculated relatively simply for a CPAP device which generates pressure at a constant level insofar as the total leak is easily calculated and $L_P$ is a function of pressure provided the mask type is known. For bilevel devices $L_P$ must be calculated at every moment for the pressure value at that moment in time. The sum of the differences between the standard flow and the purge hole flow summed over the entire breath is the excess leak (EQ. 3).

$$L_{Ex} = \frac{\sum_i (F_i - L_{Pi})}{\sum \Delta t} \quad [3]$$

For an approximate square wave EQ 3 reduces to the following where $L_{PI}$ is the purge hole leak during inhalation and $L_{PE}$ is the purge hole leak during exhalation.

$$L_{Ex} = L_T - \frac{(L_{PI} t_I + L_{PE} t_E)}{t_I + t_E} \quad [3a]$$

If the pressure waveform approximates a square wave we may further separate total leak (EQ. 4) into an inhale leak portion ($L_I$) and an exhale leak portion ($L_E$) each of which exists for an inhalation time ($t_I$) and an exhalation time ($t_E$). Both $L_I$ and $L_E$ have a purge hole leak portion and an excess leak portion. We may solve for either $L_I$ or $L_E$ if we assume that they have the same ratio as the purge hole leaks (EQ. 5) whose value as a function of pressure is known a priori.

$$L_T = \frac{(L_I t_I + L_E t_E)}{t_I + t_E} \quad [4]$$

$$\frac{L_{PE}}{L_{PI}} = \frac{L_E}{L_I} \quad [5]$$

Calculation of Tidal Volume

Figure 2:
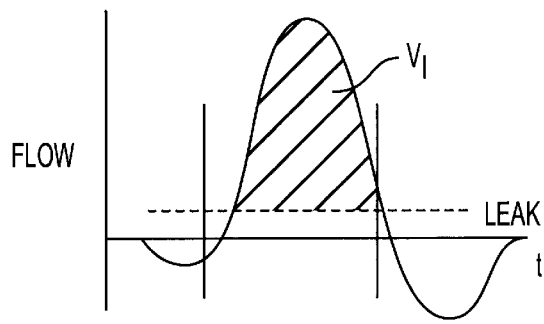
FIG. 2 shows the calculation of tidal volume by integrating the flow versus time curve for the inhalation portion of the breath.

Tidal volume is calculated by integrating the flow during the inhalation portion of the breath as shown in FIG. 2. To obtain an accurate value it is necessary to subtract off the volume due to the leak in this case, $L_I$ times $t_I$, since leak will differ between inhalation and exhalation due to the pressure difference. EQ. 6 expresses this symbolically.

$$V_I = \int_{J_i} F_i \, dt - L_I * t_I \quad [6]$$

Peak Inhalation Flow

Peak inhalation occurs during the inhalation portion of the breath. We are interested in the maximum flow into the patient so the inhalation leak needs to be subtracted from the flow.

$$F_{Peak} = F_{max} - L_I \quad [7]$$

Figure 3:
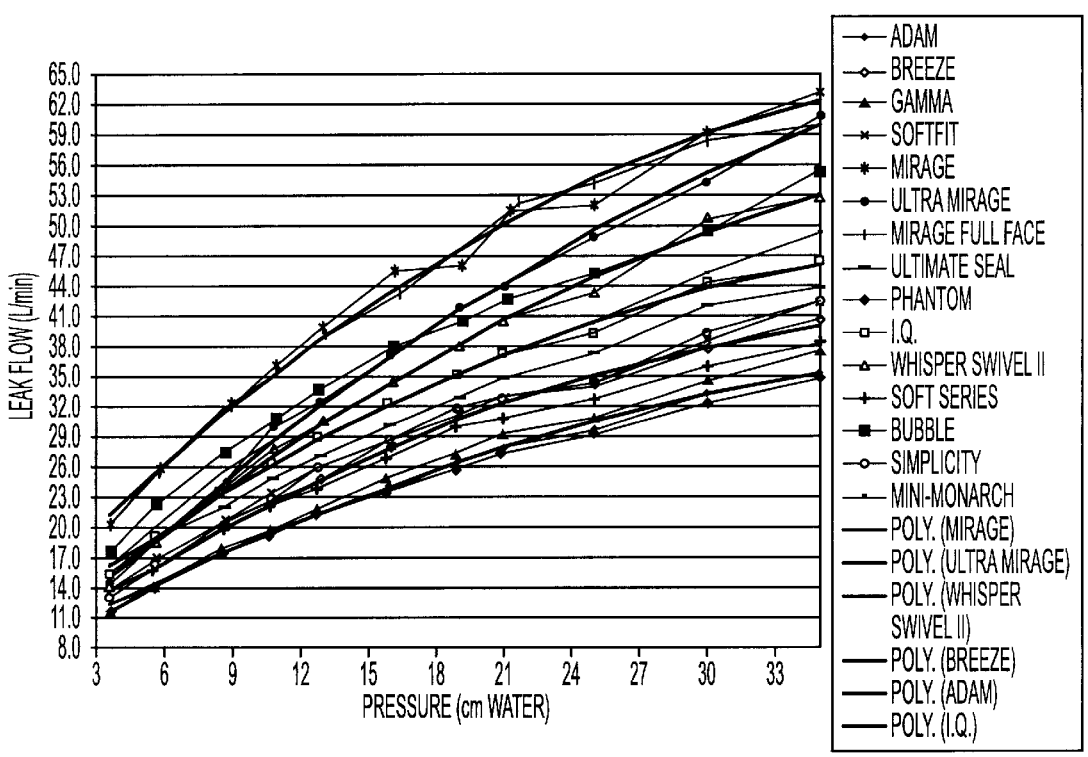
FIG. 3 shows leak flow versus pressure curves for a variety of mask types (thin lines) and composite average curves (thick lines).

It is clear for these three parameters that an accurate estimation of the purge hole leak is required. If the mask is changed, the purge hole leak changes, and it is no longer possible to obtain the leak. FIG. 3 shows purge hole leak for a variety of mask types as a function of pressure (i.e., purge hole leak profiles). It will be noted that all of these can be fit to a parabolic function of the form:

$$L_P = \text{Purge Hole Leak} = A + B*p + C*p*p$$

Where A, B and C are constants and p is the pressure. It should be remarked that the parabolic form of the function is based on convenience rather than inherent physical principles. It is known that flow leaving an orifice is proportional to the square root of pressure (Bernoulli's Equation) so that an equation of this form (i.e. $L_p = A\sqrt{Bp}$) could have been used or a higher order polynomial.

Inspection of FIG. 3 shows purge hole leak flow versus pressure curves for a selection of extant masks suitable for bilevel or CPAP therapies. It will be evident from this graph that the properties of these masks can be approximated by a multiplicity of curves (in this case the six bold curves shown in FIG. 3) without undue loss of precision at typical pressures. These curves may each be approximated by a mathematical function (e.g., a polynomial) or may exist as a multiplicity of lookup tables (e.g., arrays). Consequently it is useful to develop a means to select between these curves.

Figure 6:
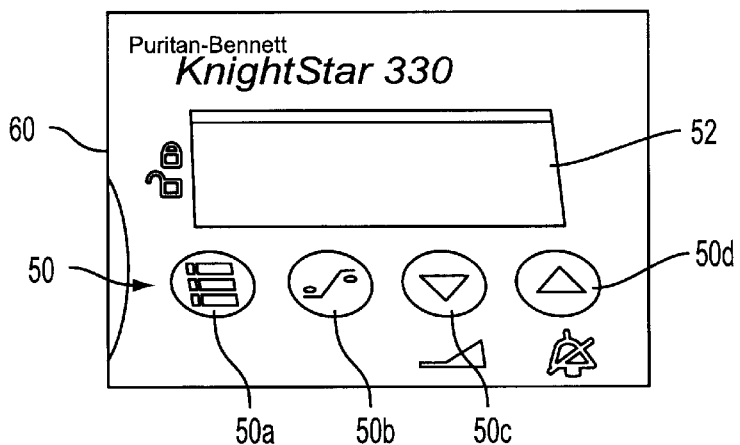
FIG. 6 shows the keypad and screen from a typical device.

Gas flow generator 12 preferably includes an external panel 60 mounting display device 52 and controls 50 as shown in FIG. 6. Display device 52 is shown herein as a 4-line liquid crystal display (LCD) of the type commonly used in a typical bilevel flow generator; however, any type of conventional display can be used including, by way of example, LCD, LED or CRT type displays with any number of lines, pixels or resolution. The display device can be color or monochrome. If an LCD, the display device can be backlighted. Alternatively, display device 52 can be a touch-screen display of the type that allows selections to be made by touching the screen with a finger or stylus. This could reduce or eliminate the number of controls on the control panel, if desired. Display device 52 can display information received from microcontroller 24 and/or from an external source via communication port 46.

Figure 4:
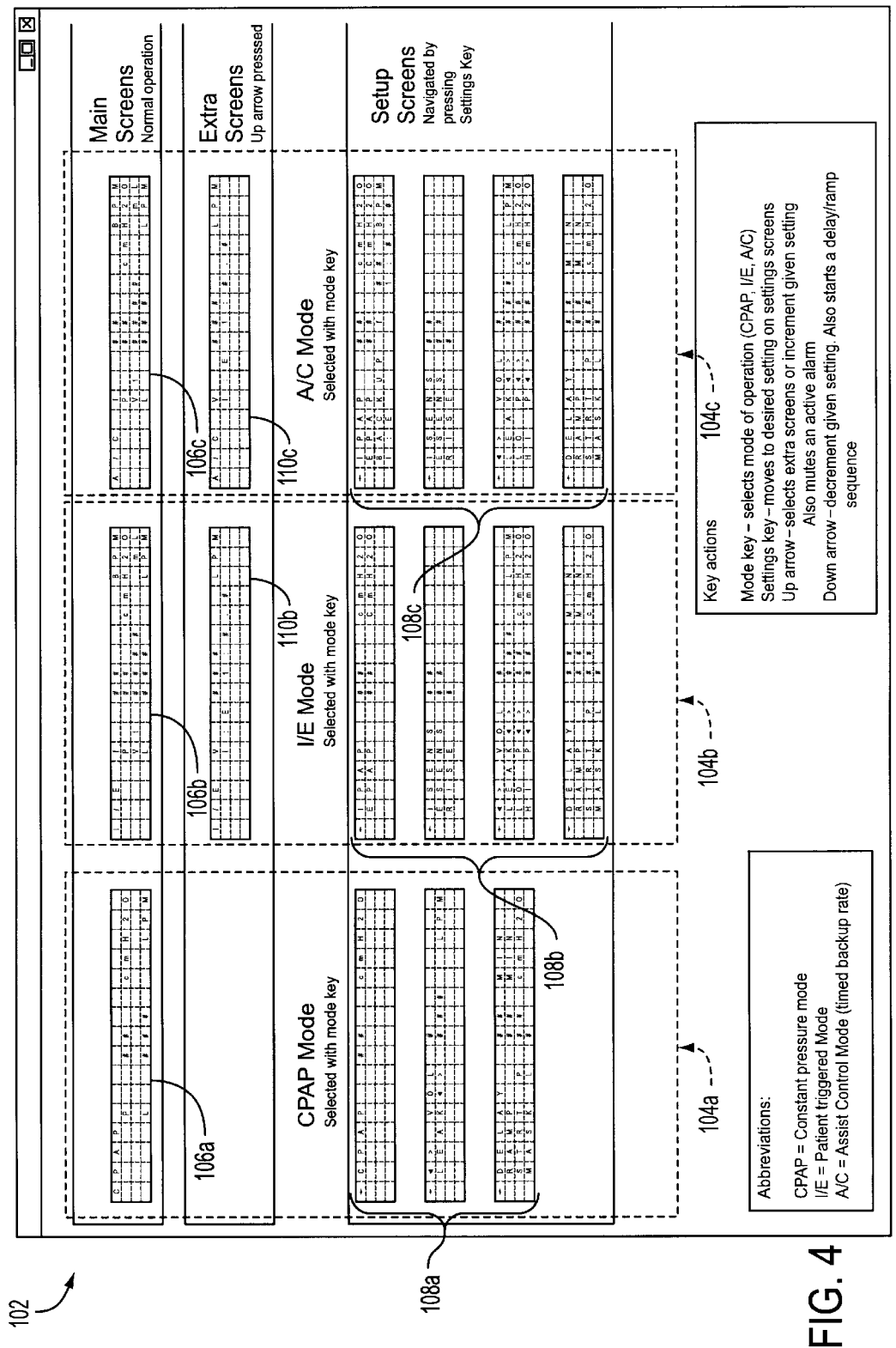
FIG. 4 shows a menu structure for a 4 line×16 character LCD display. The last line of the display labeled MASK L allows multiple mask leaks to be set.

FIG. 4 shows a preferred menu structure 102 for a typical 4-line LCD display. Menu structure 102 is made up of three submenu structures (104a, b and c) corresponding to constant pressure (CPAP), patient triggered (I/E), and assist control (A/C) operating modes, respectively. Each submenu structure includes a main screen (106a, b or c), and set-up screens (108a, b or c). The I/E and A/C submenu structures include extra screens (110b and c) as well. Main screens 106a, b and c each display the selected operating mode (i.e., "CPAP", "I/E" or "A/C"). The main screen 106a for the CPAP submenu 104a also displays pressure and excess leak. The main screens 106b and 106c for the I/E and A/C submenu structures 104b and 104c, respectively, also display frequency in terms of breaths per minute, peak pressure, tidal volume, and excess leak. Setup screens 108a, b and c each display the selected purge hole leak profile (e.g., 1, 2, 3, 4, 5 or 6) in addition to other parameters such as delay, ramp and starting pressure for all of the modes and IPEP and EPAP pressures for the I/E and A/C modes.

Figure 5:
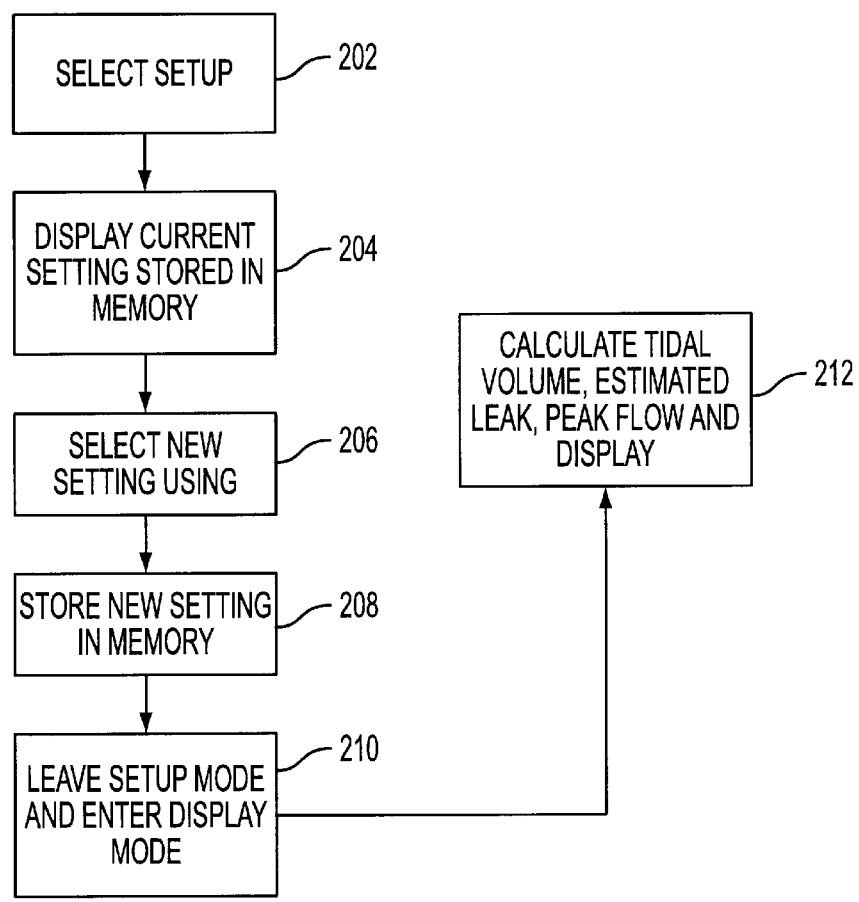
FIG. 5 shows in block diagram form the nature of the invention.

Referring again to FIG. 6, it can be seen that flow generator 12 includes a variety of controls 50 in the form of buttons or keys. These controls can be used by the operator to navigate through the menu structure displayed by display device 52 and to select various parameters such as the purge hole leak profile for a specific mask. From left to right in FIG. 6, the controls include a mode key 50a, a settings or setup key 50b, a down arrow key 50c, and an up arrow key 50d. Pressing the mode key 50a selects the mode of operation (i.e., CPAP, I/E, or A/C). Display device 52 displays the main screen corresponding to the selected mode of operation. Referring also to the flowchart in FIG. 5, it can be seen that pressing settings key 50b places the system in a setup or settings mode as indicated at 202 and causes the appropriate set of setup screens (108a, b or c) to be displayed. The current settings are displayed in the setup screens as indicated at 204. The last entry in settings mode labeled MASK L allows the user to select a value from 1 to 6 using the up and down arrow keys 50d and 50c. The value stored in memory is first displayed; it may then be changed as indicated at 206 by selecting a new value using the arrow keys, at which point it is again stored in memory (either program memory or data storage 44) as indicated at 208 and the user may leave the setting mode as indicated at 210 whereupon the function associated with the numeric entry is used in the calculation of excess leak, tidal volume and peak flow for display on device 52 as indicated at 212. Mask fit may then be optimized by examining the display while fitting the mask and working until the excess leak value becomes a minimum.

Figure 7:
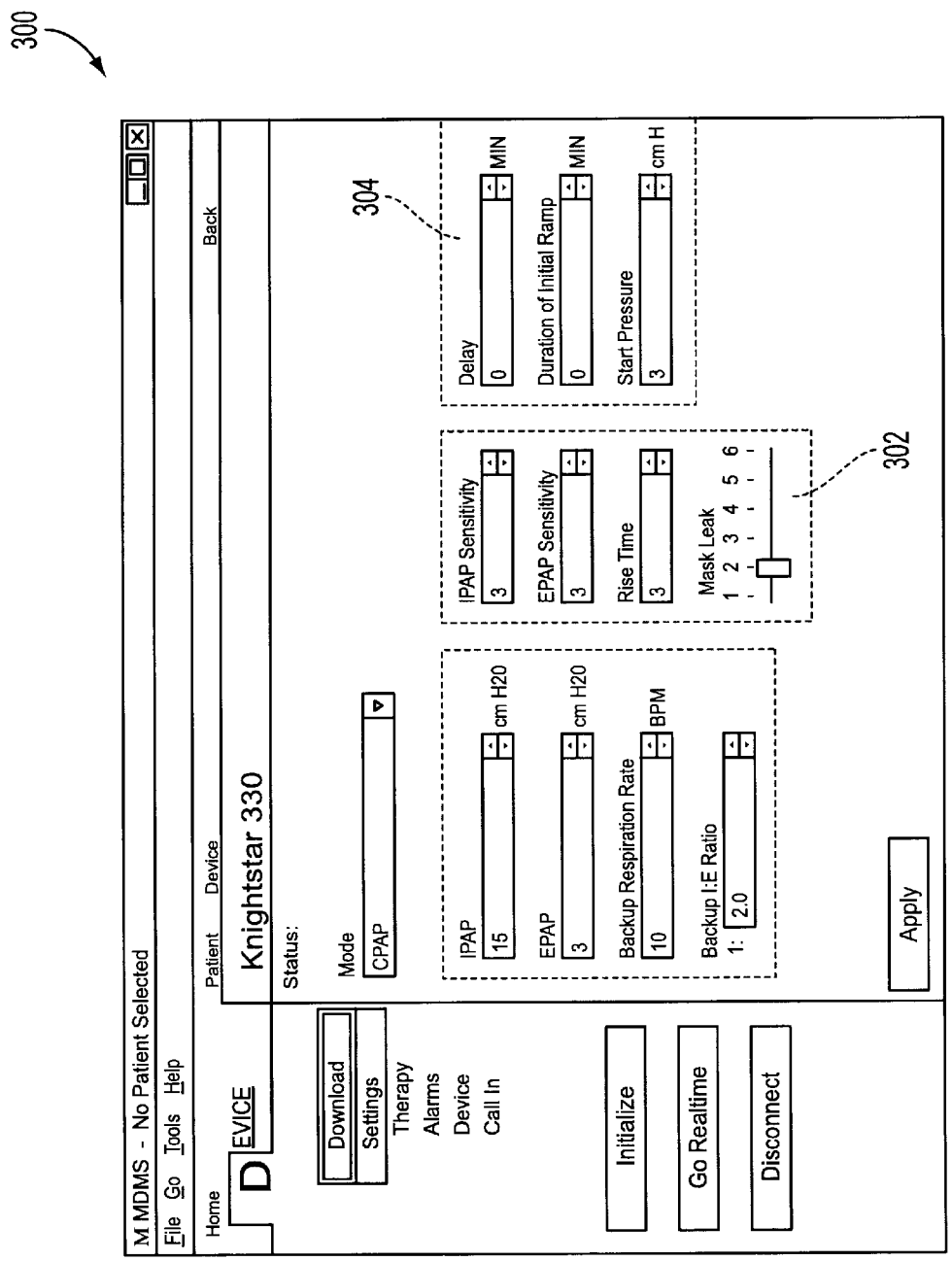
FIG. 7 shows how the mask leak setting may be set through the use of an external communication program.

Alternatively, it is contemplated that the program memory or data storage 44 may be accessed remotely through an external communication port 46 such as a standard RS232 serial communication port. Using a remote computer with appropriate communication software, the purge hole leak profile setting may be displayed on the screen of the computer in a variety of formats. FIG. 7 shows an exemplary format shown on a computer screen of a computer 300 for displaying the settings associated with the gas flow generator according to the present invention. FIG. 7 also illustrates how mask leak may be set using a typical slider control 302 displayed on the computer screen. Alternatively a text box control 304 similar to that used with the other parameters can be used as a settings means.

From the above, it will be appreciated that standard leak can be rapidly selected and conveniently changed when mask type is changed thereby obtaining accurate estimated values of tidal volume, peak flow and excess leak.

While the invention has been described in detail above, the invention is not intended to be limited to the specific embodiments as described. It is evident that those skilled in the art may now make numerous uses and modifications of and departures from the specific embodiments described herein without departing from the inventive concepts. For example, while six purge hole leak profiles have been illustrated, it will be appreciated that any number of profiles can be stored as polynomials or as values in a look-up table. It is also within the scope of the present invention to allow additional profiles to be programmed into memory and/or to edit profiles stored in memory. Programming or editing profiles can be accomplished using an external computer connected to the gas flow generator via the communications port. The profiles can be stored on the external computer or programmed into memory contained within the gas flow generator. The menu structures can be modified to include fields other than those shown and/or to delete certain fields dependent upon user needs. Also, the controls shown herein are merely exemplary of the types of controls that can be used to select the mode, purge hole leak profile, etc. Other types of controls such as push-buttons, switches, knobs, keypads, and touch-screens can be used. If desired, a single control can be used to select more than one of the specified functions or parameters. The calculated values of excess leak, peak flow and tidal volume can be used by the microcontroller to vary operational parameters of the gas flow generator.

What is claimed is:

1. An apparatus for delivering a breathing gas to a patient comprising
    a blower that generates a flow of a breathing gas;
    a gas flow rate sensor positioned to sense the flow of breathing gas generated by said blower;
    a memory device containing a plurality of purge hole leak profiles corresponding to specific breathing appliances;
    means for selecting one of said plurality of purge hole leak profiles from said memory device; and
    a microprocessor programmed to calculate at least one of excess leak, tidal volume, and peak flow using a flow rate measured by said gas flow rate sensor and the selected purge hole leak profile.

2. The apparatus of claim 1, further comprising a display device in communication with said microprocessor, said display device displaying at least one of the calculated excess leak, tidal volume, and peak flow in response to a signal generated by said microprocessor.

3. The apparatus of claim 2, further comprising an external communication port in communication with said microprocessor.

4. The apparatus of claim 3, wherein said blower, said gas flow rate sensor, said memory device, said microprocessor, said display device, and said external communication port are part of a gas flow generating unit.

5. The apparatus of claim 4, further comprising a computer, wherein said gas flow generating unit is connected to said computer via said external communication port.

6. The apparatus of claim 5, wherein said computer is programmed to display at least one of the calculated excess leak, tidal volume, and peak flow in response to a signal generated by said microprocessor.

7. The apparatus of claim 5, wherein said computer is programmed to permit selection of one of a plurality of purge hole leak profiles from said memory device.

8. The apparatus of claim 4, wherein said gas flow generating unit includes a console and wherein said selecting means includes at least one control on said console.

9. The apparatus of claim 1, wherein each purge hole leak profile is a mathematical function describing purge hole leak over a range of gas pressures for a specific mask.

10. The apparatus of claim 1, wherein each purge hole leak profile is a set of purge hole leak values corresponding to a set of gas pressure values for a specific mask.

11. A method for delivering a breathing gas to a user comprising the steps of
    generating a flow of a breathing gas using a gas flow generator;
    measuring the flow rate of the breathing gas;
    selecting one of a plurality of purge hole leak profiles from a memory device, which memory device contains a plurality of purge hole leak profiles corresponding to a plurality of specific breathing appliances; and
    calculating at least one of excess leak, tidal volume, and peak flow using the measured flow rate and the selected purge hole leak profile.

12. The method of claim 11, wherein said calculating step is performed by a microprocessor disposed within the gas flow generator.

13. The method of claim 11, wherein said calculating step is performed by a computer communicating with the gas flow generator via an external connection.

14. The method of claim 11, and further comprising, after said calculating step, the step of displaying at least one of the calculated excess leak, tidal volume, and peak flow on a visual display device.

15. The method of claim 14, wherein said displaying step includes displaying at least one of the calculated excess leak, tidal volume, and peak flow on a display panel of the gas flow generator.

16. The method of claim 14, wherein said displaying step includes displaying at least one of the calculated excess leak, tidal volume, and peak flow on a computer communicating with the gas flow generator via an external connection.

17. The method of claim 11, and further comprising the steps of measuring gas pressure and determining a purge hole leak flow rate using the measured gas pressure.

18. The method of claim 11, and further comprising the step of retrieving the selected purge hole leak profile from a computer communicating with the gas flow generator via an external connection.

19. The method of claim 11, wherein each purge hole leak profile is a mathematical function describing purge hole leak over a range of gas pressures for a specific breathing appliance.

20. The method of claim 11, wherein each purge hole leak profile is a set of purge hole leak values corresponding to a set of gas pressure values for a specific breathing appliance.

* * * * *